United States Patent
Wannlund et al.

[11] Patent Number: 5,772,967
[45] Date of Patent: Jun. 30, 1998

[54] LUMINESCENCE TEST AND EXPOSURE APPARATUS

[76] Inventors: Jon C. Wannlund, 5850 Despejo Pl., San Diego, Calif. 92124; Jerry W. Smith, 2540 E. Delhi Rd., Ann Arbor, Mich. 48103

[21] Appl. No.: 237,239

[22] Filed: May 2, 1994

Related U.S. Application Data

[63] Continuation of Ser. No. 942,321, Sep. 28, 1992, abandoned, which is a continuation of Ser. No. 567,385, Aug. 14, 1990, abandoned, which is a division of Ser. No. 308,718, Feb. 13, 1989, Pat. No. 4,985,631, which is a continuation-in-part of Ser. No. 155,955, Feb. 16, 1988, Pat. No. 5,035,866.

[51] Int. Cl.$^6$ ...................................................... B01L 3/00
[52] U.S. Cl. ........................... 422/102; 422/72; 422/300; 356/244; 356/246; 436/45; 436/165; 436/177
[58] Field of Search ..................... 422/72, 102; 356/244, 356/246; 436/45, 165, 177; 435/300, 301, 808, 8, 18, 21; 472/107, 300

[56] References Cited

U.S. PATENT DOCUMENTS

| | | | |
|---|---|---|---|
| 3,681,029 | 8/1972 | Shapiro | 422/72 X |
| 3,826,717 | 7/1974 | Gilbert et al. | 435/288.4 |
| 3,902,660 | 9/1975 | Barber | 422/72 X |
| 3,971,703 | 7/1976 | Picciolo et al. | 435/8 |
| 4,076,592 | 2/1978 | Bradley | 435/301 |
| 4,153,510 | 5/1979 | Messing et al. | 435/176 |
| 4,239,853 | 12/1980 | Bradley | 422/72 X |
| 4,330,627 | 5/1982 | Thomas et al. | 435/301 |
| 4,373,812 | 2/1983 | Stein et al. | 356/246 |
| 4,431,307 | 2/1984 | Suovaniemi | 356/246 |
| 4,640,896 | 2/1987 | Farrell et al. | 422/72 X |
| 4,777,141 | 10/1988 | Calzi et al. | 422/72 X |
| 4,818,883 | 4/1989 | Anderson et al. | 250/361 C |
| 4,842,997 | 6/1989 | Carter et al. | 435/6 |
| 4,915,911 | 4/1990 | Klose et al. | 422/102 |
| 4,944,923 | 7/1990 | Heinrichs et al. | 422/104 |

FOREIGN PATENT DOCUMENTS

| | | |
|---|---|---|
| 0 106 662 | 4/1984 | European Pat. Off. . |
| 1 220 083 | 6/1966 | Germany . |

*Primary Examiner*—Timothy McMahon
*Attorney, Agent, or Firm*—Gregory Garmong

[57] ABSTRACT

Apparatus for performing and measuring chemical reactions includes a reaction test apparatus having reaction wells wherein reactants are controllably mixed, and exposure apparatus which receives and positions the reaction test apparatus adjacent a photographic film. Each of the reaction wells includes at least two reaction chambers, arranged in a side by side fashion. All but the final reaction chamber have upwardly sloping sides, so that liquid placed in one reaction chamber can flow to the next reaction chamber when the apparatus is tilted. In a preferred embodiment, the reaction wells are supported in a plate that is structurally integral with the wells but separates the wells from each other. The test plate is retained in the exposure apparatus, and liquid is controllably flowed from one reaction chamber to the next by tilting the exposure apparatus. The apparatus of the invention is particularly suited for measuring reactions that produce luminescence of short duration, as the reactants can be conveniently mixed in darkness, while the film is being exposed.

20 Claims, 9 Drawing Sheets

LUMINESCENCE TEST AND EXPOSURE APPARATUS

This application is a continuation of U.S. Ser. No. 07/942,321 filed on Sep. 28, 1992 which is now abandoned, which is a continuation of application Ser. No. 07/567,385, filed Aug. 14, 1990 now abandoned, which is a division of application Ser. No. 07/308,718, filed Feb. 13, 1989 now U.S. Pat. No. 4,985,631 which is a continuation in part of U.S. Ser. No. 07/155,955, filed Feb. 16, 1988 now U.S. Pat. No. 5,035,866, for which priority is claimed.

BACKGROUND OF THE INVENTION

This invention deals with apparatus for performing chemical reactions, and, more particularly, with self-contained reaction apparatus for performing a sequential set of chemical reactions, and monitoring the final results.

In several types of chemical and medical test procedures, a liquid such as a body fluid must be reacted with individual reactants in a sequence of related but separate chemical reactions, and then the final product analyzed. Traditionally, such procedures have been performed by placing the fluid into a reaction tube or the like, adding the remaining reactants for the first reaction, and permitting the first reaction to proceed to completion. The further reactants for the second reaction are added, and the second reaction is permitted to proceed to completion. This stepwise operation can be repeated as many times as necessary, until a final reaction product is obtained for analysis.

This approach requires considerable technical expertise by the person performing the test, since reactants must be carefully measured and added at the correct times. If any of the reactants are perishable or deteriorate with time, the person performing the testing must exercise a critical judgment as to whether the reactants are suitable for performing the test at that time. Because these types of expertise must usually be specially taught, it is not always possible to use such testing procedures at rural or remote locations, as the necessary trained personnel, reactants, and facilities are not available.

Certain types of testing procedures do not lend themselves to such wet chemical techniques. One example is a test procedure wherein the final reaction product is analyzed by a luminescence reaction. In this type of procedure, the amount of a final product is indicated by the amount of light produced in a light producing reaction, one of whose reactants is the final product of one or more prior reactions. In certain types of luminescent reactions, the light is produced within a few seconds after the reactants are mixed together. If the traditional wet chemical procedure is used, the luminescent reactants must be mixed with the final reaction product and placed within a photometer or camera that measures the light, and the light detection initiated, within no more than about two seconds, or much of the resulting light is not measured and is lost. As is apparent, attempting to add precise amounts of reactants and perform the light measurement under such time pressures is difficult, and often leads to a mistake that requires the test to be repeated. Sometimes the mistake cannot be readily detected, and erroneous results are reported. Better techniques are therefore required to utilize sequential procedures where a final product is detected with a luminescent reaction.

An example of such a testing procedure is the detection of harmful bacteria in the urine of persons by luminescence, termed a bacteriuria test. For many years, the presence of bacteria in urine has been determined by culturing experiments which take at least 24 to 48 hours to perform and may yield inaccurate results. Culturing procedures are also costly, and often cannot be accomplished at remote locations.

More recently, a testing procedure has been developed whereby the presence of bacteriuria is detected more quickly, utilizing luminescent tagging of reaction products. In such a procedure, bacteria in urine are detected by releasing the chemical adenosine triphosphate, also termed ATP, from the bacteria. The available ATP reacts with bioluminescent reactants to produce light, and the amount of light measured indicates the concentration of bacteria initially present. ATP can also be present from other, non-bacterial sources, and any such extraneous ATP is first removed from the system, before releasing the bacterial ATP. Thus, there is a first chemical reaction whereby the extraneous ATP present from all non-bacterial sources is eliminated, a second, separate chemical reaction whereby the bacterial ATP is released into solution, and finally a third reaction of the light producing reactants with the released bacterial ATP. The second and third reactions can be performed simultaneously, but the first reaction must be completed before the bacterial ATP is released. This test is direct and reliable, and relatively inexpensive.

The luminescent test for bacteriuria can be performed by conventional wet chemical procedures such as previously described, but in this form suffers from many of the drawbacks discussed earlier, and in addition must be performed in darkness so that the production of light can be measured. An automatic luminometer testing apparatus has also been developed, which permits all of the reactions to be conducted within a single analytical luminescence apparatus, and yields a quantitative measure of the bacteriuria present in the urine of a patient. This approach has significantly advanced the art of bacteriuria testing.

The luminometer testing apparatus, however, costs several thousand dollars to purchase. Its use in some circumstances, such as rural and undeveloped areas, is therefore limited. The chemicals used in the luminometer are perishable. Additionally, in many instances the use of the luminometer provides much more information than is necessary. For example, in most cases urine samples yield negative bacteriuria results. The quantitative analysis capability of the luminometer is not required as to those negative results. Furthermore, it is generally observed that positively testing patients are usually heavily positive, and there are few cases of borderline results where the urine specimen contains a bacteriuria count near the arbitrarily defined dividing line between positive and negative results. The proper treatment is often identical for all positively testing persons. That is, in the majority of instances a simple qualitative determination of negative or positive bacteriuria count in a specimen is sufficient for screening purposes, and in many cases it is sufficient for all diagnostic purposes. In the event that further quantitative study is required, then the luminometer at a central location could be used more efficiently than for general screening studies.

There is therefore a need for an apparatus and test protocol for performing qualitative or semi-quantitative tests for bacteriuria by the luminescent analysis procedure. The apparatus must permit controlled sequential chemical reactions, and specifically must permit removal of non-bacterial ATP prior to the release of bacterial ATP for luminescent detection. The apparatus should be sufficiently simple that it can be used by technicians with little training, should serve to minimize errors due to chemical deterioration or technician error, and should be inexpensive so that tests can be performed economically. The present invention fulfills this need, and further provides related advantages.

SUMMARY OF THE INVENTION

The present invention is embodied in apparatus and a process for testing specimens requiring sequential chemical reactions, using light-producing reactions to indicate the presence of a selected reactant. The luminescence is recorded on photographic film for further analysis. The apparatus is fully self contained so that the testing can be accomplished in a lighted room, can be operated with little training, minimizes the chances of error, and is economical to construct and use. With a preferred embodiment of the apparatus having multiple test wells, either one or multiple tests can be performed, and the remaining unused wells can be utilized at a later time. The apparatus thus provides excellent flexibility of use, and is adapted for use either in a busy laboratory or at remote sites.

Practice of the invention involves two separate but interrelated pieces of apparatus. The chemical reactions are performed within a reaction test apparatus, which in turn is contained within an exposure apparatus which controls the operation of the reaction test apparatus and records the light output.

In accordance with the invention, a reaction test apparatus for assessing reactions by the production of luminescence comprises two adjacent test wells, each test well including a first reaction chamber having a first upwardly sloping interior wall, a second reaction chamber disposed adjacent the top of the first upwardly sloping interior wall of the first reaction chamber, whereby tilting of the apparatus causes liquid in the first reaction chamber to flow from the first reaction chamber to the second reaction chamber along the first upwardly sloping interior wall; and a web section supporting but separating the two wells. Particular care is taken to prevent light leakage from one well to another well, as such leakage could interfere with the accuracy of the test data. Separation of the wells by the web section prevents direct transmission of light, and transmission of light through the web section itself can be reduced by placing light diffracting grooves in the web section and also incorporating a dispersion of light diffracting particles into the material of construction. The final reaction chamber, in this case the second reaction chamber, has a transparent bottom so that light produced in the final reaction chamber may be monitored from below. The test wells are supported in a support, and generally there are a plurality of identical test wells in the support.

In one particularly preferred form of the invention, a reaction test apparatus for testing a liquid therein comprises at least one test well, the test well including a first reaction chamber having a first upwardly sloping interior wall, a second reaction chamber disposed adjacent the top of the first upwardly sloping interior wall of the first reaction chamber, whereby tilting of the apparatus causes liquid in the first reaction chamber to flow from the first reaction chamber to the second reaction chamber along the first upwardly sloping interior wall, and further having a second upwardly sloping interior wall oppositely disposed to the location of the first reaction chamber, and a final reaction chamber disposed adjacent the top of the second upwardly sloping interior wall of the second reaction chamber, whereby tilting of the apparatus causes liquid in the second reaction chamber to flow from the second reaction chamber to the final reaction chamber along the second upwardly sloping interior wall, and further having a transparent bottom so that light produced in the final reaction chamber may be monitored from beneath the final reaction chamber; and a support for the test well.

As indicated, the presently preferred utilization of the reaction test apparatus is in analyzing for the presence of particular reactants by luminescence emitted during chemical reactions. In accordance with another aspect of the invention, luminescence exposure apparatus for conducting luminescence reaction tests on specimens contained within a test well in a reaction test apparatus comprises a lower housing having a flat, upwardly facing internal surface for receiving a piece of film thereupon, a fixed shutter covering the upwardly facing surface and having a plurality of openings therethrough positioned to correspond to the locations of the test wells in the reaction test apparatus, biasing means on the fixed shutter for resisting the downward movement of the reaction test apparatus, when the reaction test apparatus is placed upon the fixed shutter, and a movable shutter between the internal surface and the fixed shutter; and an upper housing including translation means for controllably urging the reaction test apparatus downwardly against the resistance of the biasing means, thereby contacting the bottom of the reaction well in the reaction test apparatus with the piece of film in the lower housing.

The reaction test apparatus permits the penultimate, or next to last, chemical reaction to be accomplished in the next to last test chamber of each reaction well. When the penultimate chemical reaction is complete, the reactants are flowed into the final reaction chamber. In the final reaction chamber, the reaction products from the completed penultimate chemical reaction are reacted with the final reactants, to produce final reaction products. These final reaction products are then measured by an appropriate technique, preferably photographic recording of the luminescence produced in the last test chamber.

In some forms of the reaction test apparatus, there are two reaction chambers, while in other forms there are three reaction chambers, and the approach is readily extended to even more reaction chambers. In each variant of the apparatus, a test liquid is reacted in a test chamber for a selected length of time and then flowed to the next test chamber, until the reacted liquid reaches the final test chamber and its properties or characteristics are measured.

In the preferred bioluminescent bacteriuria analysis, a urine specimen is added to the first reaction chamber containing reactants to release non-bacterial ATP into solution and to eliminate the non-bacterial ATP from solution. This release and elimination reaction typically requires about 10 to 60 minutes to complete. The urine treated to completion in the upper reaction chamber, containing only ATP within bacteria, then is flowed to the final reaction chamber by tilting the apparatus so that the liquid flows along the surface and into the final reaction chamber. It is necessary that the elimination of non-bacterial ATP be completed before beginning the reaction in the final reaction chamber, or erroneous results will be obtained. In the final reaction chamber the bacterial ATP is released and reacted with light-producing reagents which react with free ATP to create luminescence in an amount related to the presence of bacterial ATP in the original sample, a reaction typically requiring only about 30 seconds.

The exposure apparatus of the invention is designed to cooperate with the reaction test apparatus in accomplishing the sequential reactions and the measurement of the light emitted. The lower housing of the exposure apparatus receives a piece of film to be exposed to the light of the luminescence reaction. Preferably, the film is instant developing film, so that the results of the testing can be seen within one minute or less of completion of the exposure.

The lower housing includes the fixed shutter that covers the film, but has fixed openings therethrough corresponding to the positions of the reaction wells in the reaction test apparatus. The fixed shutter preferably includes a plurality of recesses that separate the downwardly extending test wells, to position the test wells and prevent light produced by a reaction in one test well from finding its way onto the portion of the film below another test well. The biasing means, such as a coil spring or a leaf spring, projects upwardly from the fixed shutter, to resist the downward movement of the reaction test apparatus when it is placed onto the fixed shutter. The movable shutter is placed between the fixed shutter and the film, and can be selectively opened to expose the film to the light produced in the bottom cup of the test well. The movable shutter preferable extends downward into close proximity with the film in the portions intermediate the openings through which the wells extend, to prevent light produced in one well to leak to an adjacent well.

The upper housing fits together with the lower housing to exclude light from the interior. A translation mechanism forces the reaction test apparatus downwardly against the resistance offered by the biasing means, with the bottoms of the final reaction chambers in near-contact or direct contact with the film. When the exposure apparatus is tilted, liquid flows from the first reaction chamber to the final reaction chamber (with an intermediate stop in the second reaction chamber, if it is provided). When the liquid from the first test chamber enters the final chamber, it reacts with the chemicals therein, and almost immediately produces light.

In operation of the exposure apparatus, the upper housing is first opened and the reaction test apparatus placed upon the fixed shutter of the lower housing. The placement is easy and natural to perform, as the downwardly projecting test wells of the reaction test apparatus fit easily into the recesses in the upper surface of the fixed shutter. The biasing spring on the fixed shutter prevents the reaction test apparatus from sitting in direct contact with the movable shutter that is between the fixed shutter and the film, so that the movable shutter can be readily moved at a later time.

The upper housing is then closed, and the movable shutter pulled out to expose the film to the bottoms of the test wells. The translation mechanism is operated to force the reaction test apparatus downwardly to contact the bottoms of the test wells directly to the film. Next, the exposure apparatus is controllably tilted to cause liquid to flow from the first reaction chamber into the final reaction chamber, whereupon the luminescence reaction proceeds and the resulting light is recorded on the film. After this light producing reaction is judged to be substantially complete, usually about 30 seconds, the translation mechanism is operated to release the downward force on the reaction test apparatus, so that it rises under the force of the biasing means and is no longer in contact with the film. The movable shutter is closed, and the upper housing is opened to remove the reaction test apparatus. The film is developed, either before or after the upper housing is opened, and the process is complete. The exposure apparatus is then ready for another test.

In a typical use of a preferred form of the invention for performing a number of bacteriuria tests, the laboratory technician is furnished with a reaction test apparatus having a foil cover over the tops of the reaction wells, to prevent contamination. In the most preferred form of the invention, 18 reaction wells, disposed in 3 rows of 6 wells per row, are provided in the reaction test apparatus. The technician removes the foil cover from enough of the test wells to accommodate the number of urine specimens to be tested and adds the urine samples to the upper reaction cup of each of the respective wells. Alternatively, the technician may add the urine sample to the respective test wells by puncturing the foil locally with the needle of a syringe and injecting the urine sample into the first reaction chamber. The respective urine samples are permitted to remain in the first reaction chambers for a period of time sufficient to complete the reaction of release and elimination of non-bacterial ATP, typically about 10 to 60 minutes. During this period, the reaction test apparatus may be placed within the exposure apparatus, or may remain on the laboratory bench, as this reaction within the first reaction chambers need not be conducted in darkness.

After completion of the reaction period in the first reaction chamber, the reaction test apparatus is placed onto the recess of the fixed shutter of the lower housing of the exposure apparatus, if this was not done previously. The exposure apparatus is then operated in the manner previously described. The urine solution is forced from the first reaction chamber to the final reaction chamber. The urine solution then reacts with the remaining reactants in the final reaction chamber, and light is produced if bacteriuria are present. The light is recorded on the film as a direct measure of the presence of bacteria in the initial urine specimen. The presence of bacteriuria is detected by an exposed bright spot on the film. If there are any unused test wells in the reaction test apparatus, these are recognized by their remaining foil seal, and can be later used in testing of other urine specimens.

The apparatus may be used for many other test procedures, and a few of particular interest are set forth by way of illustration and not limitation. In challenge testing, a luminescence producing organism is placed in the final reaction chamber. A solution to be tested is flowed from the first reaction chamber into the final reaction chamber, and the output of light recorded as a measure of the success of the solution in attacking the organism. In antibiotic susceptibility testing, bacteria are placed into the final reaction chamber in various dilutions, and a solution flowed into the final reaction chamber from the first reaction chamber. After a period for reaction, luminescent reagents are flowed into the final reaction chambers, and light will be produced where living bacteria remain. Toxicity testing is performed by placing light producing organisms into the final reaction chamber, and flowing a test solution into the final reaction chamber. The light output is dimmed if there is a toxic effect on the organisms. A wide variety of fluids and test samples can be studied by these and other techniques.

An important feature of the preferred embodiment of the present invention is the provision of certain key reactants in a solid form. The apyrase enzyme and somatic release reagent packaged in the first reaction chamber are provided in a solid form, as are the light producing reactants, bacterial release reagent, bovine serum albumin, and buffering agent in the final reaction chamber. These reactants normally deteriorate in effectiveness when stored in a liquid or liquid solution form for extended periods of time. Their subsequent use may lead to error in the test results. Providing these reactants in a solid form has the important advantage of prolonging their lives in the absence of refrigeration or other means for reducing deterioration, and also eliminates the possibility of spilling. The solid reactants can be provided in a wide range of forms, such as a powder deposited within the chamber, a pellet, a solid on a carrier such as paper, and so forth. The methodology for preparing these reactants in solid form will be described subsequently.

The reaction test apparatus of the present invention can also be provided with three or more reaction chambers in each test well, if additional sequential chemical reactions are to be performed prior to the light producing reaction. For example, it is known that certain urine dilutions yield higher light outputs in the luminescence reaction. To dilute the urine after the release and elimination of non-bacterial ATP is complete, another reaction chamber is provided, so that the reacted urine is diluted in the additional reaction cup, positioned so that liquid may be flowed sequentially from reaction chamber to reaction chamber, eventually reaching the final reaction chamber. This dilution use of the invention sacrifices the advantage of using all-solid reactants, but it achieves the advantage of performing the desired dilution of the urine. The dilution solution can be formulated to contain only stable ingredients, so that the long term stability and storability of the reaction test apparatus are not lost. Using a similar approach, the apparatus of the invention can be used in other types of more complex chemical reactions and testing.

It will be appreciated that the present invention provides a highly flexible system for conducting sequential chemical reactions and then measuring the results of the reactions with a light producing reaction. The apparatus is readily provided in a kit form, with the exposure apparatus being reusable indefinitely. The test can be performed by relatively inexperienced personnel, as all reactants except the test specimen are prepackaged into the reaction test apparatus. The resulting exposed film provides a permanent record of the test results, which can be evaluated either by the technician or a doctor. The testing procedure yields qualitative or semi-quantitative results particularly useful in a screening of specimens, and can be economically used in central or remote laboratory facilities with equal ease and identical results. Complete screening of specimens is often accomplished within less than an hour, so that the results are available before the patient leaves the doctor's office. Other features and advantages of the invention will be apparent from the following more detailed description, taken in conjunction with the accompanying drawings, which illustrate, by way of example, the principles of the invention.

DETAILED DESCRIPTION OF THE PREFERRED EMBODIMENTS

Figure 5:
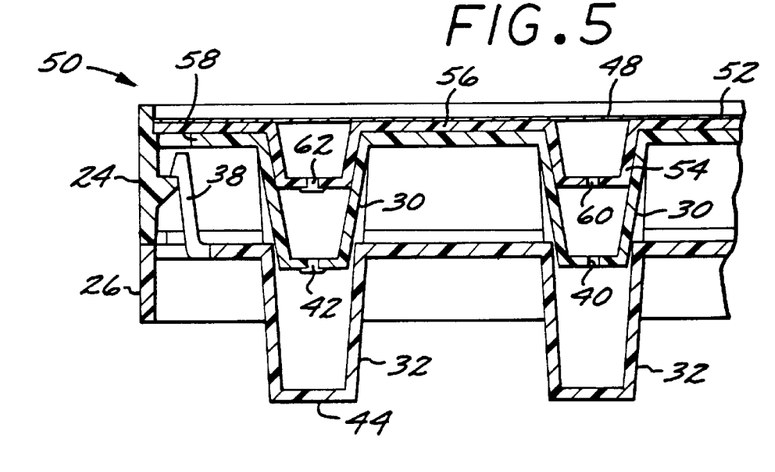
FIG. 5 is a fragmented side sectional view of a reaction test apparatus having three reaction cups in each test well.
Figure 6:
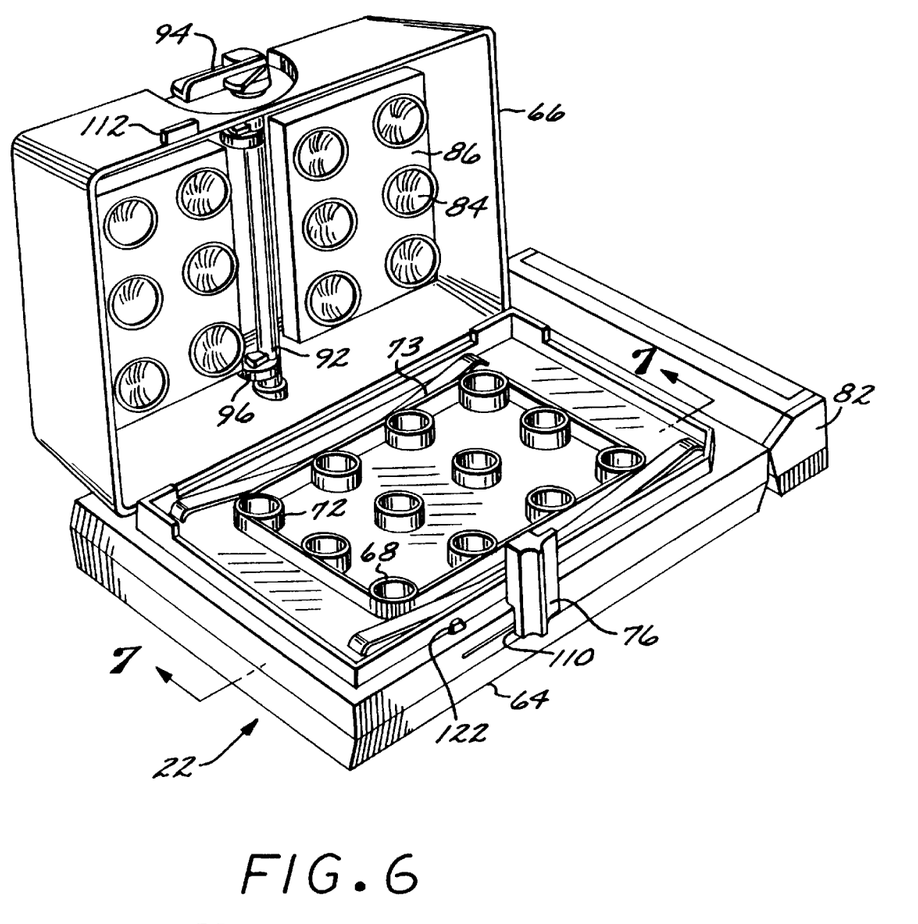
FIG. 6 is a perspective view of the exposure apparatus used in conjunction with the reaction test apparatus of FIG. 1, opened to illustrate the interior structure.
Figure 7:
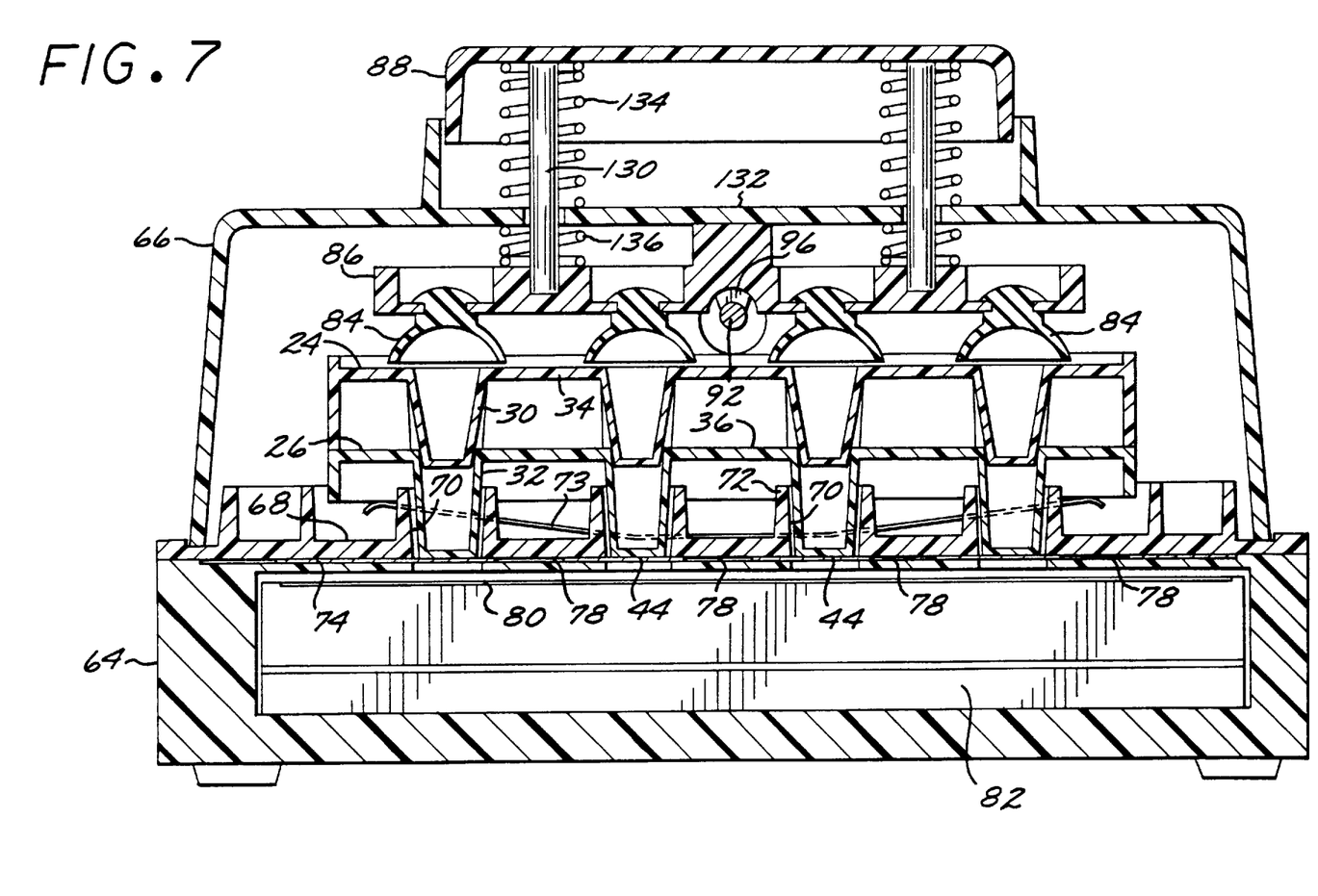
FIG. 7 is a side sectional view of the exposure apparatus of FIG. 6, taken generally along line 7—7.
Figure 8:
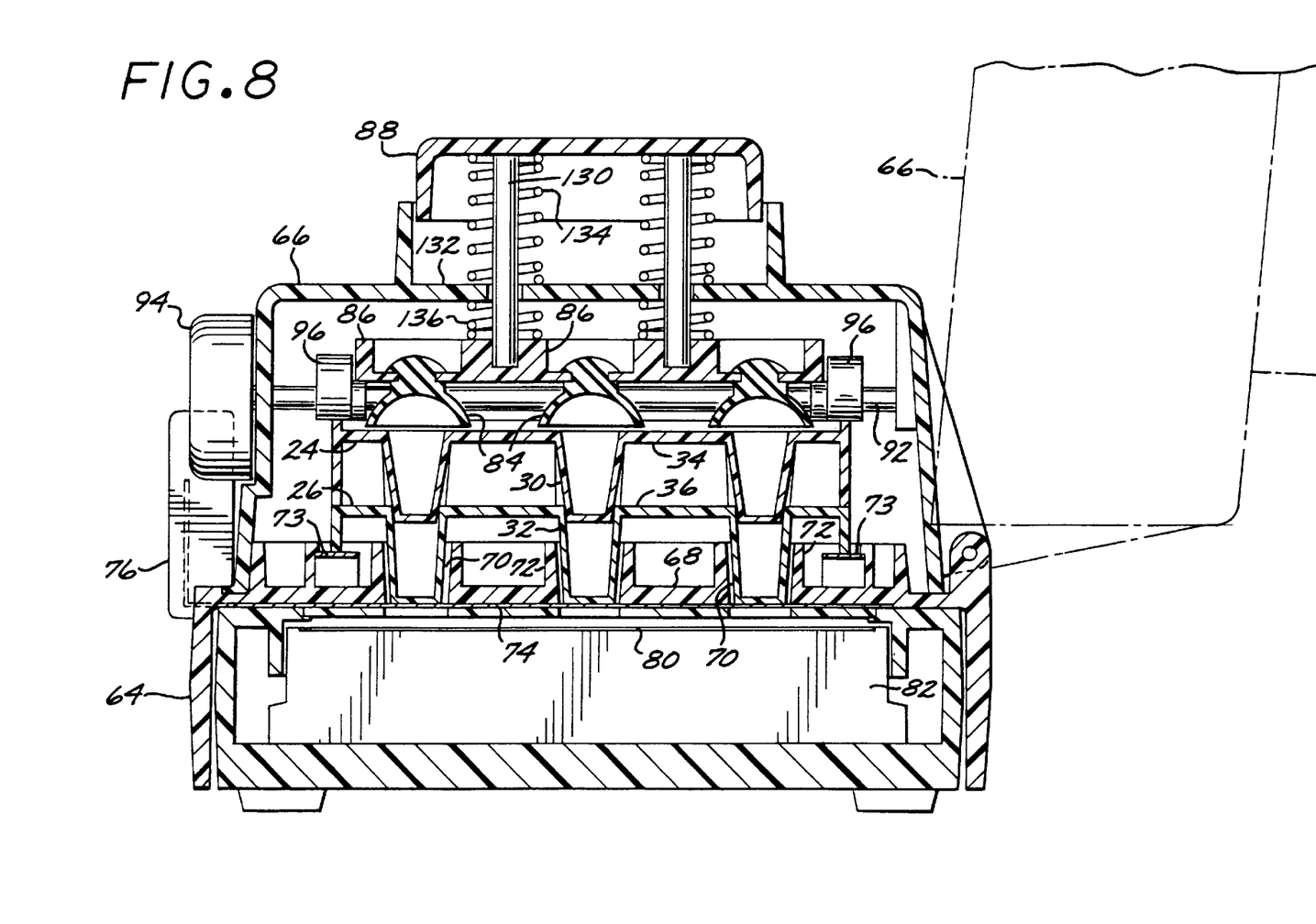
FIG. 8 is an end sectional view of the exposure apparatus of FIG. 6.

One form of the reaction test apparatus 20 is illustrated in FIGS. 1–5, and a cooperative exposure apparatus 22 is illustrated in FIGS. 6–10. The cooperative relationship between the reaction test apparatus 20 and the exposure apparatus 22 is illustrated in FIGS. 7 and 8. As shown therein, the reaction test apparatus 20 is operated by placing it within the exposure apparatus 22, closing the exposure apparatus 22, and operating the externally extending controls of the exposure apparatus 22 to effect and record chemical reactions occurring within the reaction test apparatus 20.

Figure 1:
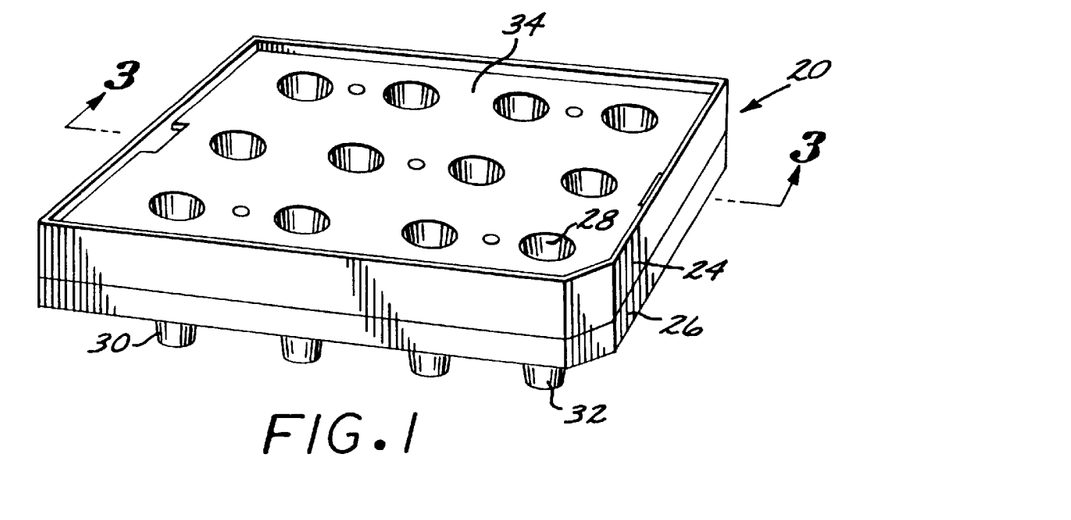
FIG. 1 is a perspective view of a first embodiment of a reaction test apparatus.
Figure 2:
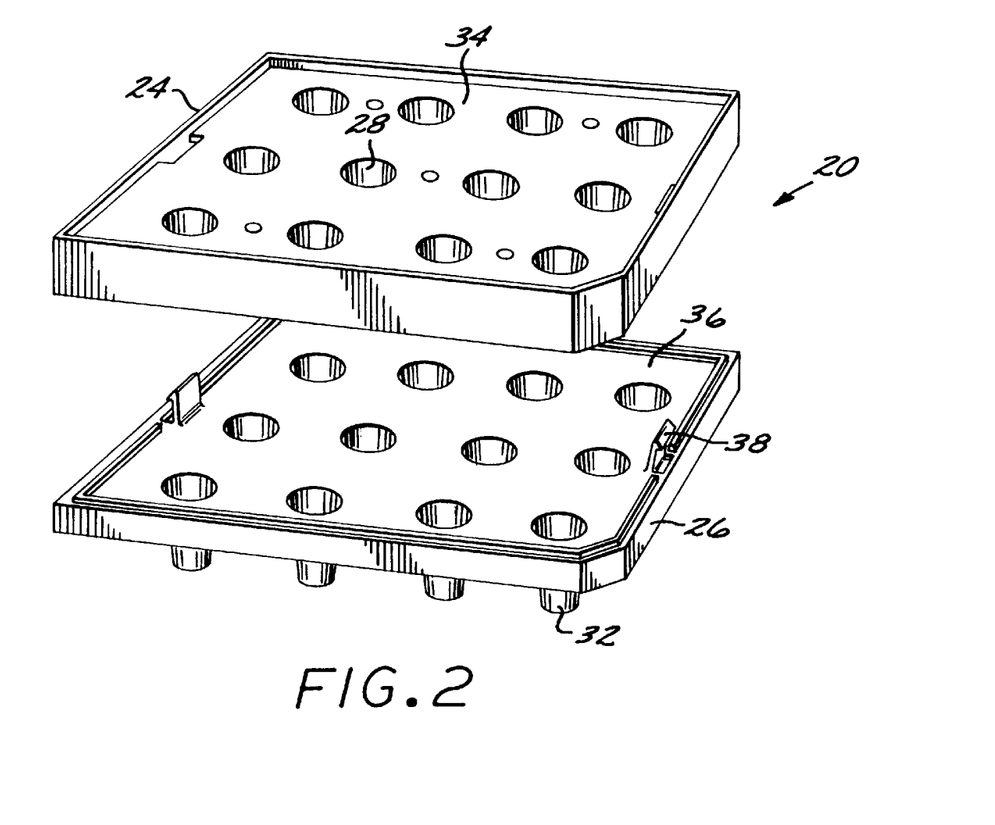
FIG. 2 is an exploded perspective view of the reaction test apparatus of FIG. 1.
Figure 3:
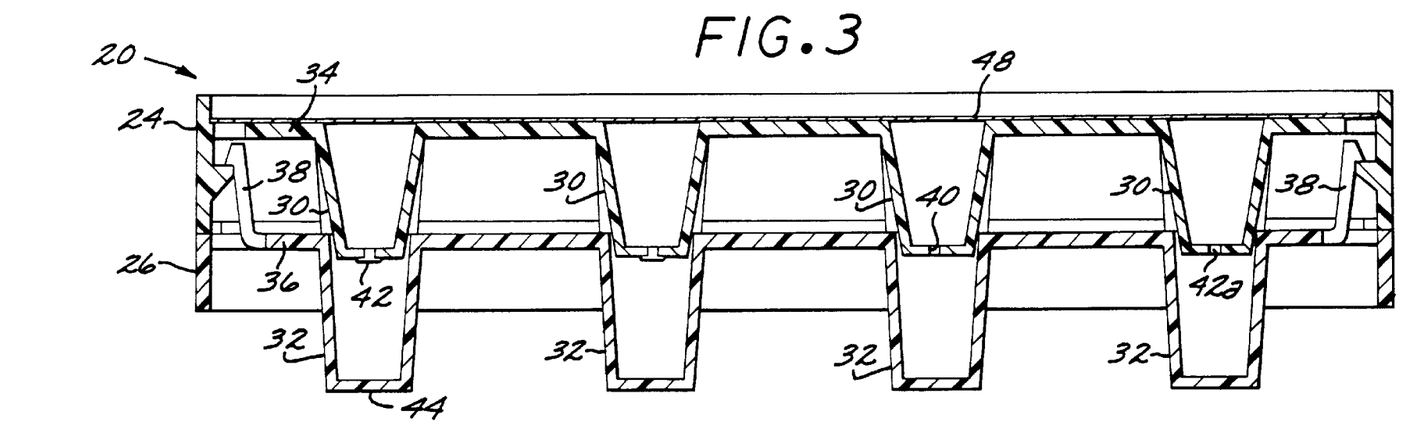
FIG. 3 is a side sectional view of the reaction test apparatus of FIG. 1, taken along line 3—3.
Figure 4:
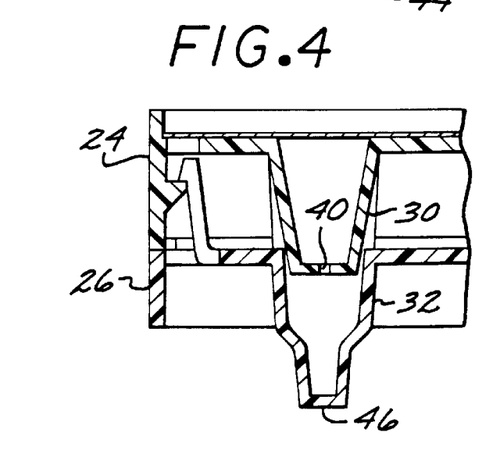
FIG. 4 is a fragmented side sectional view like that of FIG. 3, except illustrating an alternate configuration of the lower reaction cup.

FIG. 1 illustrates generally the reaction test apparatus 20, while FIG. 2 illustrates the apparatus 20 in exploded view and FIG. 3 illustrates the interrelationship of the elements within the apparatus 20. The reaction test apparatus 20 includes an upper plate 24 and a lower plate 26 which include a plurality, preferably 12, of test wells 28. The upper plate 24 and the lower plate 26 are preferably each one-piece molded plastic structures, although it would be possible to use an alternate structure wherein the test wells 28 were fabricated as separated elements and pressed into bores in the plates 24 and 26.

As illustrated in FIGS. 2 and 3, each test well 28 includes an upper reaction cup 30 and a lower reaction cup 32. One upper reaction cup 30 for each test well 28 is molded into the upper plate 24, and one lower reaction cup 32 for each test well 28 is molded into the lower plate 26. The shape of the upper plate 24 is defined, and the upper reaction cups 30 are held in position, by an upper web 34 that forms the skeleton of the structure of the upper plate 24. Similarly, the shape of the lower plate 26 is defined, and the lower reaction cups 32 are held in position, by a lower web 36 that forms the skeleton of the structure of the lower plate 26.

Each cup 30 and 32 has an open top and sides that taper inwardly from the top to the bottom of the cup. The inward taper permits the upper reaction cups 30 to be nested within the lower reaction cups 32 during assembly of the reaction test apparatus 20. The two plates 24 and 26 are dimensioned to be otherwise conformable. The reaction test apparatus 20 can therefore be assembled in the manner illustrated in FIG. 2, by slipping each upper cup 30 downwardly into the corresponding lower cup 32, and then joining the upper plate 24 to the lower plate 26, either permanently or releasably.

Preferably, the plates 24 and 26 are releasably joined, as an aid in assembly of the apparatus 20. The joining mechanism includes a pair of molded catches 38, one on each end of the lower plate 26. Each catch 38 is a tab having a tapered upper end extending upwardly from the outside end of the lower web 36, and is dimensioned to be slightly flexible. The upper plate 24 is releasably secured to the lower plate 26 by slipping it downwardly into secure contact with the lower plate 26, so that the catch 38 on each end captures and snaps closed over the respective end of the upper web 34. The upper plate 24 can be disassembled from the lower plate 26, if desired, by manually pulling each catch 38 outwardly and lifting the upper plate 24 upwardly.

As more fully illustrated in FIG. 3, the upper reaction cup 30 has an orifice 40 in the bottom thereof. The orifice 40 is closed by a removable plug 42, preferably a small amount of chemically inert silicone laboratory grease. An increased internal pressure within the upper reaction cup 30, as controllably applied by the exposure apparatus 22, causes the plug 42 to be ejected. Ejection of the plug 42 opens the orifice 40, so that any liquid therein falls downwardly into the lower reaction cup 32, which is positioned directly below the upper reaction cup 30 in their nesting relationship. In some instances, surface tension of the liquid in the upper reaction cup 30 is sufficient to prevent it from flowing through the orifice 40, as illustrated at numeral 42a of FIG. 3. In those instances, no plug 42 is provided. (In FIG. 3, the two leftmost upper reaction cups 30 are illustrated with the plugs 42 in place, while the two rightmost upper reaction cups 30 are illustrated without plugs.)

The lower reaction cup 32, also illustrated in FIG. 3, has no orifice therein, but instead has a flat bottom 44 adapted to be placed in close contact with the surface of a photographic film. In another embodiment illustrated in FIG. 4, the lower wall of the lower reaction cup 32 is further tapered into a flat bottomed tubular section 46, to achieve direction of the light produced by a chemical reaction within the cup 32 into a smaller area as defined by the size of the bottom of the tubular section 46, and thereby increase its intensity within that area.

In typical use of the reaction test apparatus 20, chemical reactants are placed into the reaction cups 30 and 32 prior to shipment to customer laboratories. The preferred reactants and the method of their preparation will be described subsequently. To retain the chemical reactants in the cups 30 and 32, and to prevent their contamination, a foil cover 48 is preferably sealed over the top of the upper plate 24. In use, the foil cover 48 is removed or punctured when a particular test well 28 is used, and this physical disruption of the foil cover 48 serves as an indicator of which test wells 28 have been used.

In another embodiment illustrated in FIG. 5, a reaction test apparatus 50 contains an upper plate 24 and a lower plate 26, which are preferably identical to those previously described, and in addition a top plate 52. The top plate includes a plurality of top reaction cups 54, supported by a top web 56. The top reaction cups 54 are conformably arranged to nest with the upper reaction cups 30 in the upper plate 24. With the use of this embodiment in mind, the upper plate 24 is fabricated with an upwardly projecting lip 58. The top web 56 is dimensioned to fit snugly within the bounds of the lip 58 and be retained therein. As illustrated in FIG. 5, the top plate 52, upper plate 24, and lower plate 26 are conformably nested and retained together in the manner described.

The top reaction cup 54 has an orifice 60 in the bottom thereof similar to that in the bottom of the upper reaction cup 30, so that removal of a plug 62 from the orifice 60 allows liquid to flow out of the top reaction cup 54 into the upper reaction cup 30. The addition of the top reaction cup 54 permits another chemical reaction or procedure to be performed prior to the reaction in the upper reaction cup 30, and prior to the reaction in the lower reaction cup 32. As is apparent, the principle of multiple reaction cups can be extended to four, five, or more vertically aligned reaction cups in a single reaction test apparatus.

The reaction test apparatus 20 or 50 is preferably used in conjunction with the exposure apparatus 22 illustrated in FIGS. 6–10. As illustrated in FIG. 6, the exposure apparatus 22 includes a lower housing 64 and an upper housing 66 which is hingedly joined along one side to the lower housing 64. The hinged arrangement permits the upper housing 66 to be closed with the lower housing 64 to form a light tight container, and to be opened to insert a reaction test apparatus therein in the manner to be described.

The sectional view of FIG. 7 shows the apparatus 22 with the upper housing 66 in the closed position and a reaction test apparatus 20 in place therein. The upwardly facing portion of the lower housing 66 is a fixed shutter 68 having a plurality of openings 70 therethrough. The positions of the openings 70 are selected to correspond to the positions of the test wells 28 of the reaction test apparatus 20, so that each test well 28 is positioned directly above one of the openings 70. A collar 72 surrounds and projects upwardly from each opening 70. The collars 72 are cylindrical and have inner diameters sufficiently large that the test wells 28 fit slidably within the collars 72. The cooperative engagement between the test wells 28 of the reaction test apparatus 20 and the collars 72 of the exposure apparatus 22 permits the reaction test apparatus 20 to be comfortably engaged into the exposure apparatus 22.

A biasing arrangement on the upper surface of the fixed shutter 68 resists the downward movement of the reaction test apparatus 20 when it is placed into contact on the top of the fixed shutter 68. The biasing arrangement preferably includes a pair of biasing springs 73, on opposing sides of the upper surface of the fixed shutter 68. The biasing springs 73 are preferably leaf springs, as illustrated, or may be coil springs or any other suitable type. The biasing springs 73 cooperate with other portions of the mechanism in translation of the reaction test apparatus 20 within the exposure apparatus 22, in a manner to be described subsequently.

A movable shutter 74 is slidably disposed below the fixed shutter 68, and can be moved relative to the fixed shutter with an external shutter handle 76. In the preferred embodiment, the movable shutter 76 has a plurality of openings 78 therethrough. The openings 78 have the same pattern and spacing as the openings 70 in the fixed shutter 68, but each of the openings 78 is physically offset from its corresponding opening 70 in the direction of the movement of the movable shutter 74. Consequently, when the movable shutter 74 is closed, the movable shutter 74 blocks the openings 70, and there is no continuous light path through the two shutters 68 and 74. When the movable shutter 74 is opened by grasping the handle 76 and pulling the movable shutter 74 outwardly, at the full extension the openings 78 line up with the openings 70, and there is a line of sight path through the two shutters 68 and 74 at each of the openings 70 and 78. This preferred approach is for a short throw design for the movable shutter 74. Alternatively, the movable shutter can be made a solid piece, requiring that it be withdrawn fully to create a line of sight path.

Within the lower housing 64 below the movable shutter 74 is a piece of photographic film 80, which is exposed to the test wells 28 when the movable shutter 74 is opened to align the openings 70 and 78. Preferably, the film 80 is of the instant developing type, and there is provided an instant processing film pack 82 to accomplish the developing of the film 80. The preferred type of film 80 has an ASA rating of 20,000, which is available in packs of eight instantly processing prints from Polaroid Corporation as its Type 612 film. The film pack 82 is self contained, and need only be inserted into the conforming lower housing 64 with the film 80 below the movable shutter 74.

The upper housing 66 includes a mechanism for applying pressure to the tops of the test wells 28 when the exposure apparatus 22 is closed. An arched rubber diaphragm 84 is positioned above the location of each of the collars 72, as determined when the apparatus 22 is closed, but separated from the collars so that the diaphragms 84 contact and cover the tops of the test wells 28 when the apparatus 22 is closed with a reaction test apparatus 20 in place. The rubber diaphragms 84 are mounted on a diaphragm support 86, which has a pressure bar 88 portion thereof extending through the top of the upper housing 66 through a light-tight seal. The pressure bar 88 is supported on the diaphragm support 86 by rods 130. Coil springs 134 and 136 position the diaphragm support 86 so that the diaphragms 84 are loosely in contact with the tops of the upper reaction cups 30, until an external downward force is applied to the pressure bar 88. The upper spring 134 reacts between the pressure bar 88 and a portion of the housing 66, indicated by numeral 132. The lower spring 136 reacts between the portion of the housing 132 and the diaphragm support 86. The lower spring 136 normally has a higher spring constant than the upper spring 134, to restore the position of the pressure bar 88 after operation is complete.

A downward force applied to the pressure bar 88 against the resistance of the spring 134 brings the diaphragms 84 into close, sealing contact with the tops of the upper reaction cups 30, and continued downward force compresses the air inside the diaphragms 84 and the upper reaction cups 30. A sufficient downward force builds up sufficient pressure within the upper reaction cups 30 to pop out the grease plug 42 from the bottom of the orifice 40, so that liquid in the upper reaction cups 30 can flow through the orifice 40 and into the lower reaction cups 32. Where there is no grease plug 42 because surface tension of the liquid is sufficient to prevent liquid from otherwise flowing through the orifice 40, the downward pressure is sufficient to overcome the surface tension and force the liquid of the test specimen downward through the orifice 40. The diaphragms 84 provide a structurally simple, reliable method for moving the liquid reactants from the upper reaction cup 30 into the lower reaction cup 32.

The luminescent chemical reactions that produce the light recorded on the film 46 produce relatively faint light, and several techniques are utilized to use that light as effectively as possible. The tubular sectioning 46 of the lower reaction cup 32, discussed previously, is one such technique. A very fast film, such as the ASA 20,000 film previously discussed, is typically used. Another technique to utilize the light most fully is to contact the bottom 44 of the lower reaction cup 32 directly to the film 80 during exposure. This can be accomplished by translating the reaction test apparatus 20 downwardly to bring the bottom 44 of the lower reaction into contact with the film 80, after the movable shutter 74 is opened. An externally operable translation mechanism is provided for this purpose.

The translation mechanism includes a rod 92 mounted horizontally through the center of the upper housing 66 and fixed at each end in a bearing surface, so that the rod 92 can be rotated. The rod 92 extends outside of the upper housing 66 through a light-tight baffle, and ends in a translation control lever 94. Inside the upper housing 66, the rod has a cam lobe 96 on each end thereof, positioned over the top of the reaction test apparatus 20. Operation of the lever 94 rotates the cam lobe 96 into contact with the top of the reaction control apparatus 20, and continued rotation forces the reaction control apparatus 20 downwardly toward contact with the top of the fixed shutter 68, against the biasing force of the biasing springs 73. At full operation of the cam lobe 96, the reaction test apparatus 20 is forced downwardly sufficiently far that the bottoms 44 of the lower reaction cups 32 directly contact the film 80. This downward movement of the reaction test apparatus 20 is done only when the movable shutter 74 is opened, so that the lower reaction cups 32 can be contacted to the film 80. It is in this position that the exposure pressure bar 88 is operated and the exposure of the film 80 is completed. After exposure is complete, the lever 94 is operated in the reverse direction to rotate the cam lobe 96 to release the pressure on the reaction control apparatus 20, so that the reaction control apparatus 20 moves upwardly under the influence of the biasing spring 73. With the apparatus 20 in its upward position, the movable shutter 74 can be closed.

As is apparent, the movable shutter 74, lever 94, and pressure bar 88 must be operated in the correct sequence for the exposure of the film to be properly completed. To reduce the chances for operator error, an interlock system has been incorporated into the exposure apparatus 22 to prevent an incorrect sequence of operations. The interlock system is best seen by reference to FIGS. 7–10.

Figure 9:
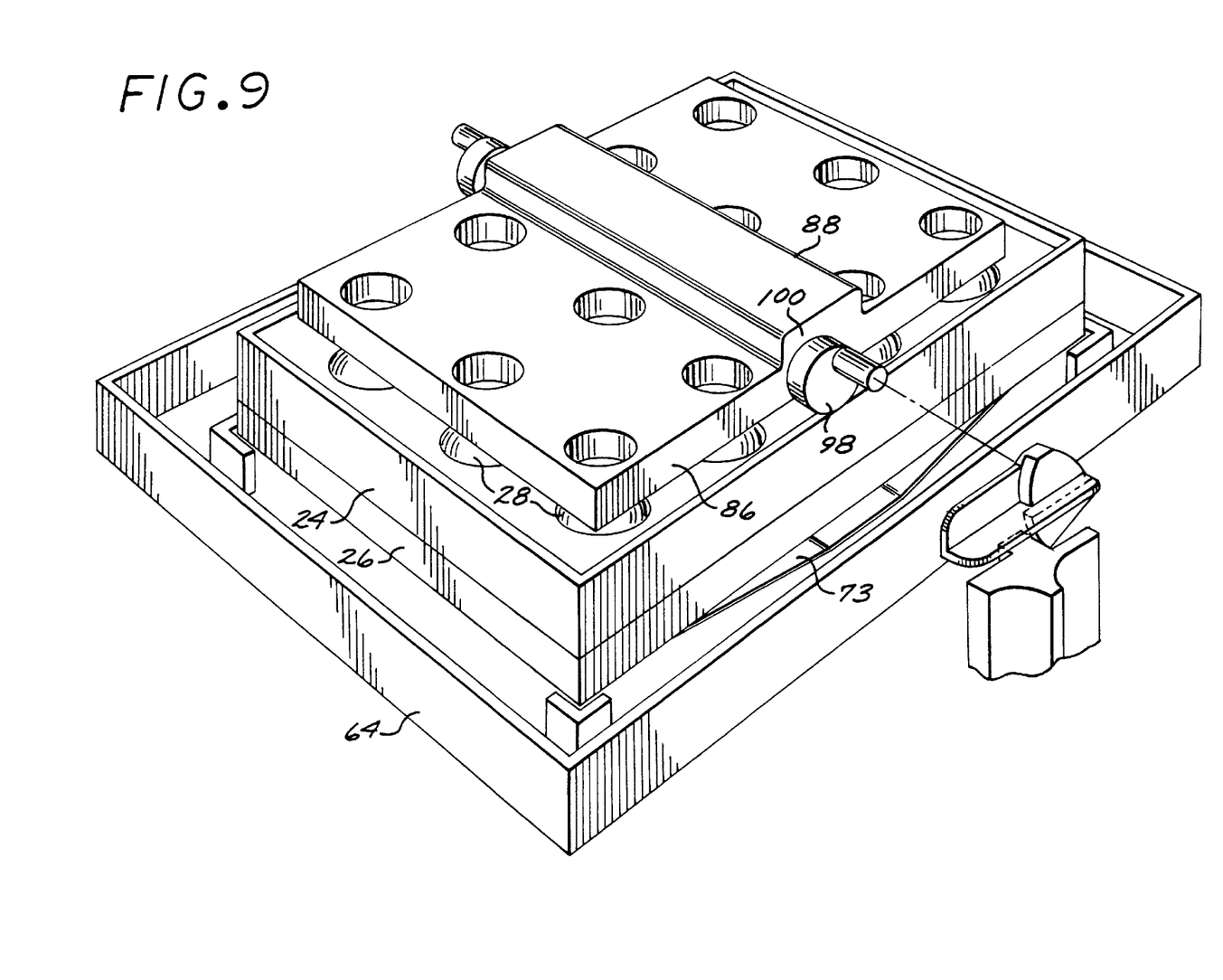
FIG. 9 is a perspective view of the exposure apparatus of FIG. 6, with the top cover broken away to illustrate the internal mechanism.

The shutter handle 76 projects from the side of the lower housing 64 in a position to contact a side of the translation control lever 94 in the manner illustrated in FIG. 9. The control lever 94 cannot be rotated to translate the reaction test apparatus 20 downwardly unless the shutter handle is moved to the outward position to align the openings 70 and 78. The shutter handle 76 is attached to the shutter 74, which cannot be moved unless the upper housing 66 is closed to the lower housing 68 to form a light-tight seal therewith, due to an interlock between the two parts. When the shutter handle 76 is operated to open the shutter 74, a notch 110 in the handle 76 engages a tab 112 on the upper housing 66 to lock the upper housing 66 closed, thereby preventing its inadvertent opening at any time at which the film is exposed.

Figure 10:
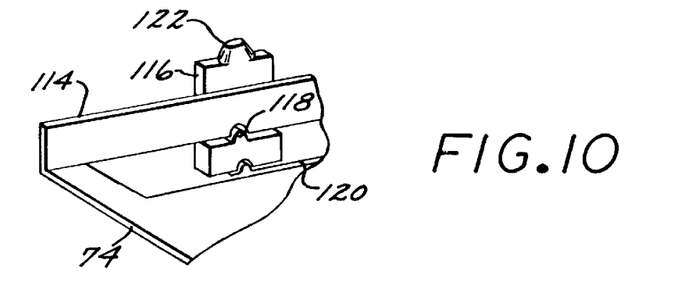
FIG. 10 is a perspective view of a detail of the locking mechanism of the exposure apparatus.

The slide interlock, illustrated in FIG. 10 in a reverse angle view, is effected by a slide lock 116 mounted in the lower housing and biased upwardly by a spring 120. In the locked position illustrated in FIG. 10, a locking tab 118 on the slide lock 116 engages a conforming recess in a locking rail 114 that projects upwardly from one side of the movable shutter 74, preventing movement of the shutter 74. An extension 122 extends upwardly from the top of the slide lock 116, through an opening in the housing 64. The wall of the upper housing 66 depresses the extension 122 when the upper housing 66 is closed, thereby depressing the slide lock 116 against the force of the spring 120 to unlock the shutter 74. As the shutter handle 76 is moved to open the shutter 74 after being so unlocked, the upper housing 66 is locked closed by the engagement between the shutter handle 76 and the tab 112. After the film exposure is complete, the housing 66 can be opened only when the shutter 74 is returned to its closed position by operation of the handle 76, where it is again locked closed by the slide lock 116. This same movement of the handle 76 unlocks the upper housing 66 so that it may be opened, by disengagement of the tab 112.

Mounted on the rod 92 is a pressure bar locking cam 98. The cam 98 is a part-circle cam that contacts the bottom side of the diaphragm support 86 when the translation control lever 94 is in the position that the reaction test apparatus 20 is in its upward position. Thus, in this position, the pressure bar 88 is locked into place and cannot be inadvertently operated. When the translation control lever 94 is operated to force the reaction test apparatus 20 downwardly, the locking cam 98 is rotated away from the diaphragm support 86, and the pressure bar 88 (connected to the diaphragm support 86) can be operated. After exposure of the film 80, the translation control lever 94 is operated to raise the reaction test apparatus 20, again locking the diaphragm support 86 in place. With the translation control lever 94 in this position, the shutter handle 76 can again be operated to close the shutter 74 and unlock the upper housing 66, so that the reaction test apparatus 20 can be opened. This interlock mechanism prevents an incorrect sequence of operations of the external control apparatus.

In the most preferred use, the present invention is used for analysis of the bacteriuria content of urine samples. This test depends upon the reaction of bacterial ATP with luminescent reagents, to produce light that is measured on the film 80. There are two sources of ATP in a urine sample, bacterial and non-bacterial sources. The objective of the preferred bacteriuria test is to measure bacterial sources only. In the preferred test, the ATP in non-bacterial sources is first removed so that it cannot adversely affect the test results, and then the ATP in bacterial sources is released and reacted with the luminescent reagents.

In this test procedure, the upper reaction cup 30 contains a release reactant to lyse somatic cells, releasing non-bacterial ATP therefrom. The release reactant does not affect the bacterial ATP, which remains bound to the bacteria. The release reactant is Triton X100 detergent (polyoxyethylene ether). The upper reaction cup 30 also contains an enzyme elimination reactant (preferably apyrase) to dephosphorolate the non-bacterial ATP to adenosene monophosphate, also known as AMP, which is not measured by the subsequent luminescent assay. The preferred elimination reactant is apyrase enzyme.

To prepare the reagent used in the upper reaction cup 30, about 0.16 units of solid apyrase enzyme and about 100 microliters of 0.2 percent aqueous solution of Triton X100 detergent liquid are mixed with 0.5 milligrams of bovine serum albumin. This mixture is added to the upper reaction cup 30 and freeze dried.

Upon completion of the reaction between the non-bacterial ATP in the urine specimen with the reactants in the upper reaction cup 30, the reacted urine specimen is passed through the orifice 40 into the lower reaction cup 32 for the second reaction. In the lower reaction cup 32, the bacterial ATP is released, and reacted with luminescent reagents. The result is light produced in proportion to the bacterial ATP, with the amount of light measured indicating the amount of bacterial ATP present in the urine specimen.

To prepare the solid material for the lower reaction cup, the following ingredients are mixed together: about 100 microliters of a 0.005 percent to 0.6 percent concentration aqueous solution of a chemical bacterial releasing agent (such as polyoxyethylene ether, hexachlorophene, chlorohexadine, or dimethylsulfoxide), about 10 to 100 micrograms of firefly luciferase enzyme, about 15 micrograms of solid D-luciferin, about 10 microliters of a 10 millimolar magnesium chloride luminescent cofactor, about 0.5 milligrams of bovine serum albumin, and a N-2-Hydroxyethylpiperadine-N'-2-ethanesulfonic acid buffer to bring the pH of the solution to 7.75. The solution is added to the cup 32 and freeze dried.

Urine specimens are then tested in the manner discussed previously. The urine sample is added to the upper reaction cup 30 and reacted therein for a period of time sufficient to eliminate all non-bacterial ATP, which usually requires about 1–10 minutes. The reaction test apparatus 20 is placed into the exposure apparatus 22, the apparatus 22 is closed to form a light-tight enclosure, and the shutter handle 76 is operated to lock the apparatus 22 closed and open the movable shutter 74. With the shutter handle 76 moved to the position with the shutter 74 opened, the interlocked translation control lever 94 is operated to force the reaction test apparatus 20 downwardly and place the bottom 44 of the lower reaction cup 32 in contact with the film 80. At this point, the urine sample is still in the upper reaction cup 30, and there has been no light output. Rotation of the control lever 94 unlocks the diaphragm support 86 and pressure bar 88 in the manner previously described, and the pressure bar 88 can then be operated to press the rubber diaphragms 84 against the tops of the upper reaction cups 30. The pressure thereby created in the upper reaction cup 30 ejects the grease plug 42, so that the liquid in the upper reaction cups 30 flows into the lower reaction cups 32. The liquid mixes with the release reagent and luminescent reagent in the cup 32, producing light in an amount related to the amount of bacterial ATP released. The light is recorded on the film 80. The light producing reaction begins within about 2 seconds or less after operation of the pressure bar 88, and is completed after no more than 30 seconds.

After a sufficiently long time that the light-producing reaction is essentially complete, typically about 30 seconds, the translation control lever 94 is operated to release the downward pressure on the reaction test apparatus 20 so that it moves upwardly to its uppermost travel under the urging of the biasing spring 73. The shutter handle 76 is closed to end the exposure and unlock the upper housing 66. The instant film pack 82 is operated to develop the film 80, either before or after the shutter handle 76 is operated. After the film is developed, typically 60 seconds for Type 612 ASA 20,000 speed instant film, the test results on the film are ready for viewing. The reaction test apparatus 20 (if there are any remaining unused test wells) and exposure apparatus 22 are ready for further testing. The presence of any previously unused test wells 28 of a particular reaction test apparatus 20 is immediately apparent upon visual search for undisrupted portions of the foil cover 48, as the foil cover 48 above used test wells 28 is torn or disrupted during insertion of the specimen into the test well 28.

The embodiment of the reaction test apparatus described to this point operates by application of a positive pressure to force liquid from one superimposed cup downwardly into another cup. The structure of the exposure apparatus is dictated in part by the need to provide the positive pressure by external application. Liquid flow from one portion of the reaction test apparatus to another portion can also be accomplished solely by gravity-induced flow, and in another embodiment the reaction test apparatus is structured for this operation. The exposure apparatus has a structure permitting this mode of transfer.

Figure 11:
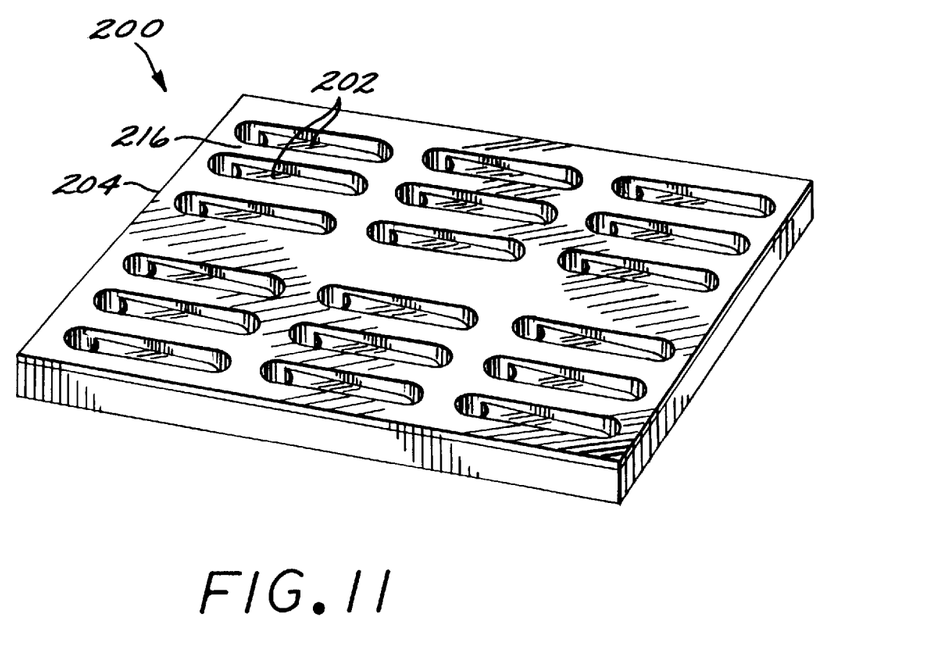
FIG. 11 is a perspective view of another embodiment of the reaction test apparatus.

FIG. 11 illustrates one form of a reaction test apparatus 200 wherein the flow of liquid is accomplished completely by gravity feed, without the application of a positive pressure. A plurality of test wells 202, preferably 18 wells arranged in three rows of six wells per row, are formed in a pour plate 204.

Figure 12:
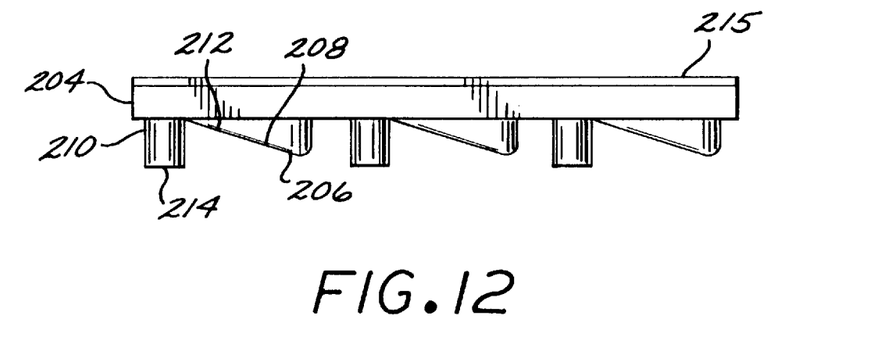
FIG. 12 is a side elevational view of the reaction test apparatus of FIG. 11.
Figure 13:
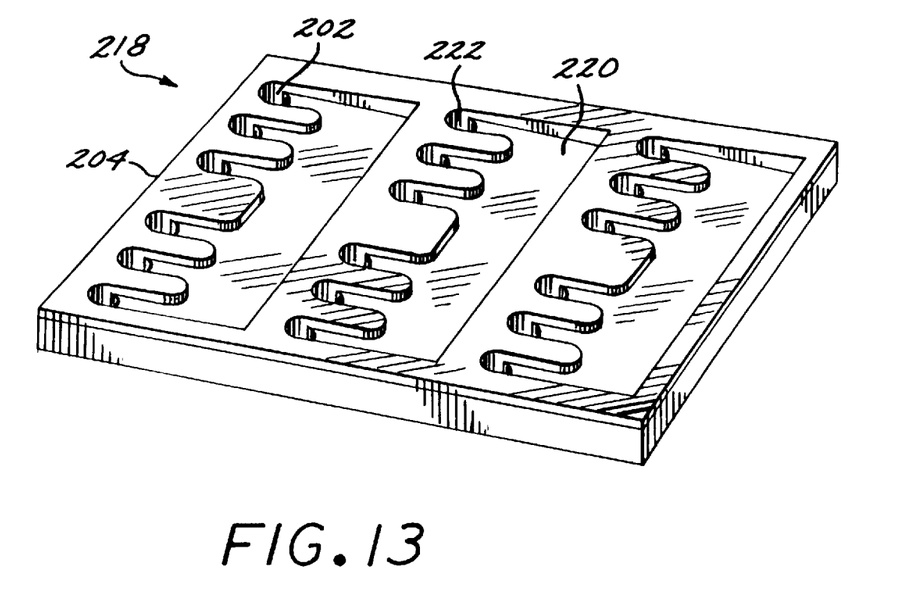
FIG. 13 is a perspective view of a variant of the reaction test apparatus of FIG. 11.
Figure 14:
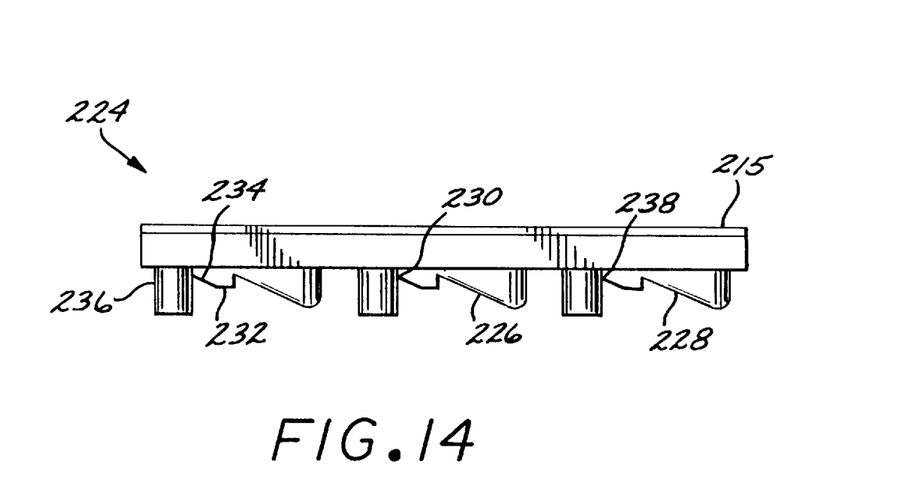
FIG. 14 is side elevational view of another variant of the reaction test apparatus of FIG. 11.

The structure of each well 202 is seen more clearly in FIG. 12. The test well 202 includes a first reaction chamber 206 extending downwardly from the pour plate 204. The first reaction chamber 206 has on one side an upwardly sloping interior wall 208 that slopes upwardly and outwardly from the bottom of the chamber 206. A final reaction chamber 210 is positioned adjacent the first reaction chamber 206, near the top end 212 of the upwardly sloping interior wall 208. The final reaction chamber 210 is illustrated as a generally cylindrical cup with an open top and a closed, flat bottom 214. In use, a liquid specimen is placed into the first reaction chamber 206 and reacted with a first reactant. When sufficient time has passed for the first reaction to be as complete as required, then one end of the pour plate 204 (in the illustrations of FIGS. 11 and 12 the right end) is displaced upwardly so that the pour plate 204 is rotated (counterclockwise in FIGS. 11 and 12). The reacted liquid specimen in the first reaction chamber 206 flows along the sloping interior wall 208 and thence into the final reaction chamber 210, where it reacts with a second reactant. In the preferred luminescence reaction described previously, light is emitted and measured through the flat bottom 214 of the final reaction chamber 210. A foil seal 215 covers the top of the test apparatus. The seal 215 is shown in FIGS. 12 and 14, but is removed in FIGS. 11 and 13 for clarity.

The transmission of light between adjacent wells must be reduced as much as possible, because such stray light from a well in which a strong reaction occurs can result in false readings in adjacent wells that perhaps do not contain as strong a light emitting reaction. Several techniques are used in the reaction test apparatus of the invention to prevent light from passing between adjacent wells.

To prevent light produced in one of the final test chambers 206 from being mistakenly recorded as light produced from another of the chambers 206, the pour plate 204 provides a support 216 between each of the chambers 206, which supports but also separates the adjacent wells. Transmission of light directly from one well to an adjacent well is therefore greatly reduced, particularly where the exposure apparatus places an opaque wall in the separating region created by the support 216. This approach is to be contrasted with that used for test apparatus that is not used for luminescence testing, where for cost reasons the adjacent wells are not separated.

However, there remains the possibility that light will be piped through the material of the supporting pour plate 204 from one well to another. An effective approach to reducing the light transmission through the plastic itself, which is operable in the reaction test apparatus of the invention as well as other types of reaction test apparatus used in luminescence measurements systems, is to provide grooves 280 in a web 282 portion of the pour plate 204 that extends between the test wells 28 in the manner illustrated in FIG. 15. A number of opposing but offset grooves 280 extending inwardly into the web 282 diffract light traveling within the plastic to prevent it from being transmitted through the plastic from one well to the adjacent well. When the light beams from a well strike the sloping walls of the grooves, they are diffracted away and out of the support structure, and therefore do not reach the adjacent test well.

Another aid to preventing erroneous measurements due to light transmitted through the plastic from one well to another is to include a dispersion 284 of opaque dispersing particles within the plastic. The plastic is made thin in the region of the bottom of the flat bottoms 214 of the wells 202, and therefore the dispersing particles have little influence. However, when interposed in the longer light transmission path between adjacent wells, the particles aid in reducing light transmission between wells. A preferred approach is to mix into the plastic, prior to molding, on the order of 5 percent by weight of carbon particles.

Figure 15:
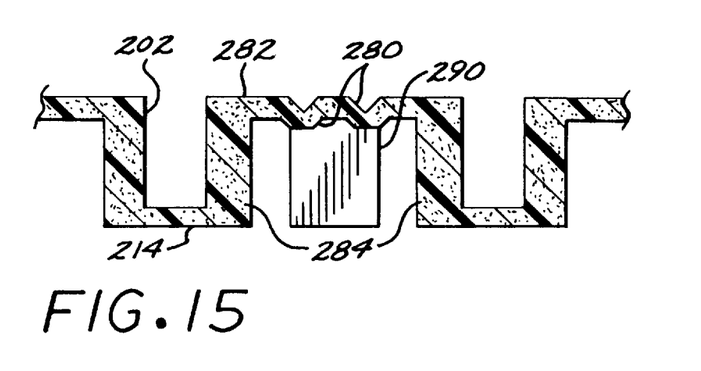
FIG. 15 is a side elevational view of a portion of the pour plate support and two adjacent wells.
Figure 16:
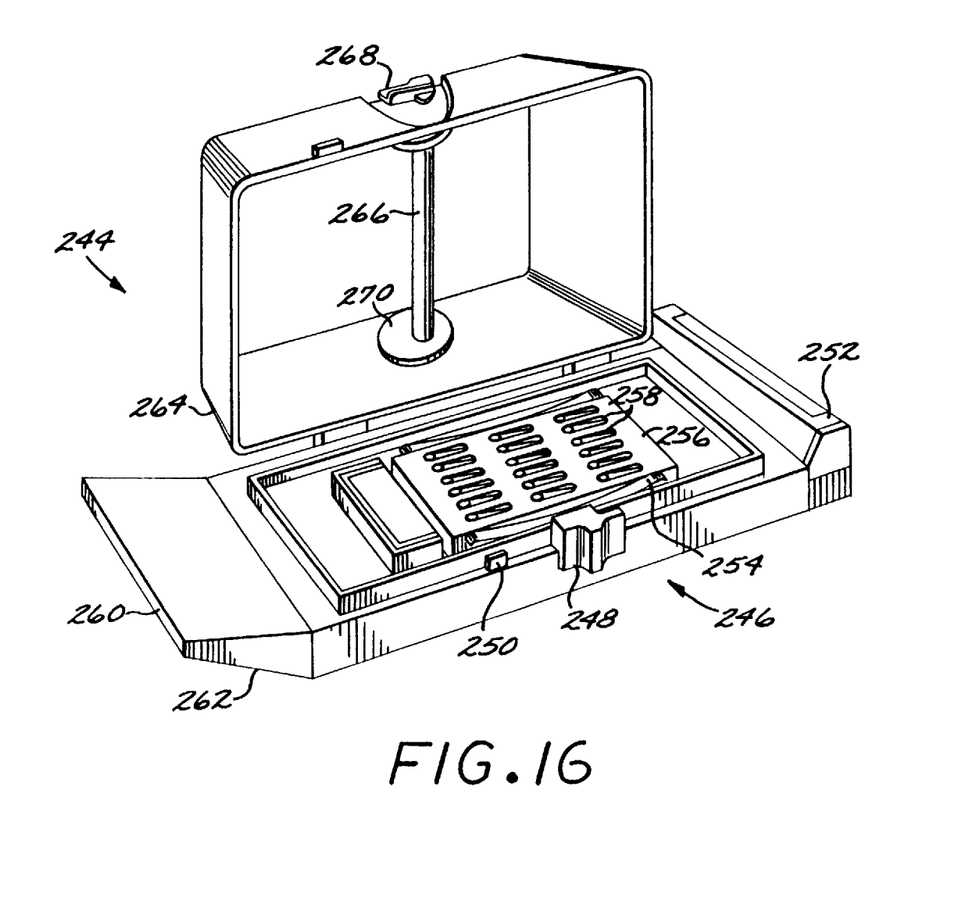
FIG. 16 is a perspective view like that of FIG. 6, of an exposure apparatus used in conjunction with the reaction test apparatus of FIGS. 11–14.

FIG. 15 also illustrates the previously discussed approach of providing the support 216 that separates the adjacent wells. The web 282 is part of the support 216 that spaces the wells 202 apart from each other. Light cannot easily travel directly, in a straight line, between the adjacent wells 202 due to their spacing. Moreover, in practice there is ordinarily provided an opaque wall 290 in the exposure apparatus 244, which fits into the separating space between the wells 202. The wall 290 ensures that no light passes directly through the space between the wells.

In the embodiment of FIGS. 11 and 12, there is a single individual first reaction chamber for every final reaction chamber. In a variant test apparatus 218, illustrated in FIG. 13, there is a single first reaction chamber 220, which receives the liquid specimen. There are a plurality of individual final reaction chambers 222 that each receive a portion of the reacted liquid specimen upon tilting and rotating of the pour plate 204. The structure of the test wells 202 in this embodiment is otherwise essentially the same as previously described. This type of apparatus is useful where the liquid sample is to be uniformly reacted in the first reaction chamber, and then reacted with individual final reactions in the final reaction chamber.

In yet another embodiment, illustrated in FIG. 14, each test well 202 includes three reaction chambers rather than two, as in the previously described embodiments. The test well 202 of an apparatus 224 includes a first reaction chamber 226 having a first upwardly sloping interior wall 228. Adjacent a top end 230 of the wall 228 is a second reaction chamber 232, positioned so that liquid flowing along the wall 228 can pour into the chamber 232. The second reaction chamber 232 has a second upwardly sloping interior wall 234 that is preferably oppositely disposed across the chamber 232 from the top end 230 of the wall 228. A final reaction chamber 236 is positioned adjacent a top end 238 of the wall 234. The final reaction chamber 236 is generally cylindrical with a flat bottom or a shaped bottom to concentrate light onto an underlying photographic film, in the manner previously described. There is a wall in the pour plate 204 between each of the final reaction chambers 236, and the grooves and dispersion of particles are preferably provided to prevent leakage of light between adjacent test wells.

All of the embodiments of FIGS. 11–14 utilize only gravity to move fluid from one reaction chamber to another. An exposure apparatus 244, illustrated in FIG. 15, suitable for conducting the photographic recording of the test results using these embodiments is generally similar in most respects to the apparatus 22 previously described and used in conjunction with the pressure-activated reaction test apparatus 20. However, the rubber diaphragms, pressure bar, and related structure is omitted as unnecessary for the exposure apparatus 244.

As shown in FIG. 15, the apparatus 244 includes a lower housing 246 having an internal structure identical to the lower housing 64. A shutter handle 248, extension 250, film pack 252, and bias spring 254 have the same placement and function as the corresponding elements in the lower housing 64. A fixed shutter 256 is placed and oriented in a manner similar to the fixed shutter 68, except that it has a plurality of conforming recesses 258 therein to receive the downwardly projecting portions of the test wells 202 of the pour plate 204 that cooperates with the apparatus 244 in the making of measurements of liquid specimens.

The lower housing 246 has a housing extension 260 extending from the end of the housing 246 nearest the final chambers of the last row of test wells. The housing extension is a solid piece having an upwardly inclined lower surface 262 that has an angle with the horizontal preselected to aid in the transfer of liquid from one chamber to another in the test wells. In use, the apparatus 244 (with the cover closed and reaction test apparatus in place) is placed upon a flat support surface and then rotated by pushing the housing extension 260 downwardly. The extension 260 is pushed downwardly until the lower surface 262 touches the support surface, and at that point further rotation is prevented. The apparatus 244 is constructed such that the angle of the lower surface 262 to the horizontal is greater than the angle of any of the upwardly sloping interior walls of the pour plate with the horizontal, so that the rotation necessary for liquid transfer is achieved.

An upper housing 264 is similar to the upper housing 66, except that it has no pressure control mechanism. There is a translation control mechanism that operates in a manner like that of the apparatus 22. A rod 266 extends across the interior of the housing 66, and can be turned by an external translation control lever 268. Rotation of the lever 268 and the rod 266 causes two cam lobes 270, one on either end of the rod 266, to rotate. These lobes 270 push downwardly against the reaction test apparatus that is inside of the apparatus 244, causing it to move downwardly against the biasing springs 254 and into contact with the film within the lower housing 246. The interlock system preventing inadvertent exposure of the film operates like that described for the exposure apparatus 22.

The exposure apparatus 244 therefore permits a user to conduct tests using a pour plate type reaction test apparatus, which achieves fluid flow within the reaction test apparatus by rotation of the pour plate and a gravity feed and does not require a positive pressure transfer.

The present approach for testing provides a mechanically non-complex, inexpensive approach for testing specimens in testing procedures requiring sequential chemical reactions, where the results are to be evaluated by recording the results of a luminescent reaction. Although a particular embodiment of the invention has been described in detail for purposes of illustration, various modifications may be made without departing from the spirit and scope of the invention. Accordingly, the invention is not to be limited except as by the appended claims.

What is claimed is:

1. An article of manufacture, comprising:
   at least two elongated test wells, each test well including
      a first reaction chamber having a first reaction chamber bottom and a first reaction chamber upwardly sloping interior wall,
      a solid, dry first chemical reactant in the first reaction chamber,
      a second reaction chamber having a second reaction chamber bottom at a lesser height than a top of the first reaction chamber upwardly sloping interior wall and a second reaction chamber upwardly sloping interior wall that slopes upwardly from the second reaction chamber bottom in an elongated direction away from the first reaction chamber, the second reaction chamber being disposed adjacent the top of the first reaction chamber upwardly sloping interior wall, whereby tilting of the article of manufacture causes a liquid in the first reaction chamber to flow along the first upwardly sloping interior wall and into the second reaction chamber,
      a final reaction chamber having a final reaction chamber bottom at a lesser height than a top of the second reaction chamber upwardly sloping interior wall, the final reaction chamber being disposed adjacent the top of the second reaction chamber upwardly sloping interior wall, whereby tilting of the article of manufacture causes a liquid in the second reaction chamber to flow along the second reaction chamber upwardly sloping interior wall and into the final reaction chamber, the final reaction chamber bottom being transparent so that light produced in the final reaction chamber may be monitored from beneath the final reaction chamber through the bottom of the final reaction chamber, and
      a solid, dry final chemical reactant in the final reaction chamber; and
   a planar support plate for the at least two test wells, the at least two test wells being arranged in and affixed to the support plate so that the bottoms of the final reaction chambers of each of the test wells extend downwardly below the support plate and are coplanar in a plane that lies parallel to the plane of the support plate, and so that the elongated directions of the at least two test wells are parallel to each other.

2. The article of manufacture of claim 1, wherein the at least two test wells and the support plate are made of a plastic.

3. The article of manufacture of claim 2, wherein the plastic has a distribution of light diffracting particles dispersed through a portion of the plastic.

4. The article of manufacture of claim 1, wherein a portion of the support between the test wells includes a web section having grooves therein to reduce the transmission of light through the support from one well to an adjacent well.

5. The article of manufacture of claim 1, further including a second chemical reactant in the second reaction chamber.

6. The article of manufacture of claim 1, wherein the bottom of the final reaction chamber is flat.

7. An article of manufacture, comprising:
   a test well, the test well including
      a first reaction chamber having a bottom and a first upwardly sloping interior wall,
      a second reaction chamber having a flat bottom disposed adjacent to, but at a lesser height than, a top of the first upwardly sloping interior wall of the first reaction chamber, the second reaction chamber having a second reaction chamber chemical therein that is reactive to produce light; and
   a planar support plate having a web section that supports the test well with the flat bottom of the second reaction chamber of the test well extending downwardly below the web section and lying parallel to the plane of the support plate.

8. The article of manufacture of claim 7, wherein a plurality of flat bottomed test wells are present and supported in the support plate, with the flat bottoms of each of the test wells extending downwardly below the web section, being coplanar and lying in a plane parallel to that of the support plate.

9. The article of manufacture of claim 7, further including apyrase enzyme in the first reaction chamber, the apyrase enzyme being in a solid, dry form.

10. The article of manufacture of claim 7, wherein the second reaction chamber chemical reactant is selected from the group consisting of luciferase, luciferin, and combinations thereof.

11. The article of manufacture of claim 7, further including
   a solid, dry chemical reactant in the first reaction chamber.

12. The article of manufacture of claim 8, wherein the test wells are arranged in a rectangular array and the second reaction chamber for each of the test wells is constructed and arranged to be supplied from the same common first reaction chamber.

13. The article of manufacture of claim 8, further including means for preventing light from passing from one of the test wells to another of the test wells through the web section.

14. The article of manufacture of claim 13, wherein the means for preventing includes at least one groove in the web section to reduce the transmission of light through the web section.

15. The article of manufacture of claim 13, wherein the means for preventing includes a distribution of light diffracting particles dispersed through the web section to reduce the transmission of light through the web section.

16. An article of manufacture, comprising:

at least two test wells, each test well being elongated in a direction lying parallel to a common direction, each test well including a first reaction chamber having a bottom and a first upwardly sloping interior wall, and a second reaction chamber having a bottom disposed adjacent to, but at a lesser height than, a top of the first upwardly sloping interior wall of the first reaction chamber, whereby tilting of the article of manufacture causes liquid in the first reaction chamber to flow along the first upwardly sloping interior wall and into the second reaction chamber, the second reaction chamber having therein a second reaction chamber solid, dry chemical reactant capable of reacting with other chemical reactants to produce light, wherein the second reaction chamber chemical is selected from the group consisting of luciferin, luciferase, and combinations thereof; and a planar support plate having a web section that supports and separates the at least two test wells, the at least two test wells being arranged in the web section so that the bottoms of the final reaction chambers of each of the at least two test wells extend downwardly below the web section and are coplanar in a plane that lies parallel to the plane of the support plate.

17. The article of manufacture of claim 16, wherein the bottom of the second reaction chamber is flat.

18. The article of manufacture of claim 16, further including a solid, dry chemical reactant in the first reaction chamber.

19. An article of manufacture, comprising:

at least two test wells, each test well being elongated in a direction lying parallel to a common direction, each test well including a first reaction chamber having a bottom and a first upwardly sloping interior wall, the first reaction chamber further including a first chemical reactant capable of reacting with other chemicals to release adenosine triphosphate, and a second reaction chamber having a bottom disposed adjacent to, but at a lesser height than, a top of the first upwardly sloping interior wall of the first reaction chamber, whereby tilting of the article of manufacture causes liquid in the first reaction chamber to flow along the first upwardly sloping interior wall and into the second reaction chamber, the second reaction chamber having therein a solid, dry second reaction chamber chemical reactant capable of reacting with other chemical reactants to produce light; and a planar support plate having a web section that supports and separates the at least two test wells, the at least two test wells being arranged in the web section so that the bottoms of the final reaction chambers of each of the at least two test wells extend downwardly below the web section and are coplanar in a plane that lies parallel to the plane of the support plate.

20. The article of manufacture of claim 19, wherein the bottom of the second reaction chamber is flat.

* * * * *